(12) United States Patent
Del Castillo

(10) Patent No.: US 8,602,058 B1
(45) Date of Patent: Dec. 10, 2013

(54) PUSHBUTTON STOPCOCK ASSEMBLY

(76) Inventor: Gil Del Castillo, Katy, TX (US)

( * ) Notice: Subject to any disclaimer, the term of this patent is extended or adjusted under 35 U.S.C. 154(b) by 632 days.

(21) Appl. No.: 12/854,798

(22) Filed: Aug. 11, 2010

Related U.S. Application Data

(60) Provisional application No. 61/233,431, filed on Aug. 12, 2009.

(51) Int. Cl.
*F16K 11/085* (2006.01)
*F16K 31/524* (2006.01)

(52) U.S. Cl.
USPC ............ 137/625.47; 137/625.41; 251/227; 251/230

(58) Field of Classification Search
USPC .......... 137/625.46, 625.47, 876, 597, 625.41; 251/230, 215, 226, 227, 129.03
See application file for complete search history.

(56) References Cited

U.S. PATENT DOCUMENTS

| | | | |
|---|---|---|---|
| 2,695,154 A * | 11/1954 | Dillman ........................ | 251/77 |
| 3,834,372 A | 9/1974 | Turney | |
| 4,003,403 A | 1/1977 | Nehring | |
| 4,116,216 A * | 9/1978 | Rosenberg ............... | 137/624.13 |
| 4,177,972 A * | 12/1979 | Legris ........................ | 251/288 |
| 4,221,238 A * | 9/1980 | Madsen ..................... | 137/627.5 |
| 4,314,586 A | 2/1982 | Folkman | |
| 4,566,480 A | 1/1986 | Parham | |
| 4,570,674 A | 2/1986 | Kaye | |
| 4,632,361 A * | 12/1986 | Callison ....................... | 251/230 |
| 4,790,512 A * | 12/1988 | Lindsay ..................... | 251/129.2 |
| 4,865,078 A | 9/1989 | Ensign | |
| 5,671,911 A * | 9/1997 | Piscitelli ................... | 251/315.14 |
| 6,585,003 B2 * | 7/2003 | Steiner et al. ............ | 137/625.47 |
| 7,341,239 B2 * | 3/2008 | Hodel et al. ................ | 251/230 |
| 8,276,833 B2 * | 10/2012 | Cheng et al. .................. | 239/447 |
| 2007/0088252 A1 * | 4/2007 | Pestotnik et al. ............... | 604/82 |
| 2008/0319401 A1 | 12/2008 | Funamura | |
| 2011/0024516 A1 * | 2/2011 | Li et al. .......................... | 239/11 |
| 2011/0226876 A1 * | 9/2011 | Xu ................................ | 239/562 |

* cited by examiner

*Primary Examiner* — Stephen M Hepperle
*Assistant Examiner* — Daphne M Barry
(74) *Attorney, Agent, or Firm* — Andrew W. Chu; Craft Chu PLLC

(57) ABSTRACT

The pushbutton stopcock assembly has a sleeve with outer ports, a body portion with inner ports, and a pushbutton to actuate a rotation of the body portion. Each outer port of the sleeve connects to a fluid passageway for the introduction of fluids, and each inner port is in fluid connection with the other inner ports. In this manner, fluids flow and travel from fluid passageways, through the outer ports, and through the inner ports. The body portion has a first end with a spring and a second end with a cam. The pushbutton abuts the second end portion of the body portion, such that depressing the pushbutton engages the cam to be cooperative with a complementary cam within the sleeve so as to rotate the body portion a set amount. Each set amount of rotation corresponds to a particular alignment of the outer ports and inner ports.

8 Claims, 3 Drawing Sheets

PUSHBUTTON STOPCOCK ASSEMBLY

RELATED U.S. APPLICATIONS

The present application claims priority under U.S. Code Section 119(e) from a provisional patent application, U.S. Patent Application No. 61/233,431, filed on 12 Aug. 2009 and entitled "PUSHBUTTON STOPCOCK ASSEMBLY".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to fluid valves. More particularly, the present invention relates to medical stopcock valves. Even more particularly, the present invention relates to pushbutton medical stopcock valves.

2. Description of Related Art Including Information Disclosed Under 37 CFR 1.97 and 37 CFR 1.98.

A stopcock is a valve used to restrict or isolate the flow of a liquid or a low pressure gas through a pipe or other fluid passageway. Stopcocks function very similar to kitchen water faucets. Stopcocks have many applications in the medical field as well as in scientific laboratories. Small plastic stopcock valve assemblies have long been routinely used in a variety of medical procedures and operations, such as metering the infusion of fluids into patients under medical care. Typically, such stopcock valve assemblies include at least a three-way type valve wherein the valve body has three or more radially-arranged ports, and an interior directional control member is rotatably arranged within the valve body for selectively closing one or more ports while opening communication between at least two other ports.

Various patents have issued in the past relating to rotor stopcock valves that are manually operated. For example, U.S. Pat. No. 4,197,876, issued on Apr. 15, 1980 to Lobdell, teaches such a fluid valve. The fluid valve has a core received in the bore of a valve body. The bore is positioned in a separate inner body spaced radially inward from and connected by support means to the main valve body so as to hasten cooling of the bore during manufacturing and thereby improve sealing of the core by reducing dimensional variations in the bore.

U.S. Pat. No. 4,314,586, issued on Feb. 9, 1982 to Folkman, describes a disposable valve. The two-piece valve incorporates a straight cylindrical seal between the valve core and body permitting limited axial movement. The valve is molded in such a manner so as to create a strong interlock between the valve ports and to eliminate heavy sections of plastic adjacent to the sealing area of the valve.

U.S. Pat. No. 4,566,480, issued on Jan. 28, 1986 to Parham, teaches a medical stopcock valve assembly. The medical stopcock valve assembly has a valve body with extending fluid-directing tubes at least some of which have a female Luer lock fitting adapted to receive a Luer lock cap. When not in use, the medical stopcock valve is provided with a blind portion for receiving and storing a cap when it is out of use. In one form, the blind portion is formed as a female Luer lock fitting. Alternatively, recessed blind portions may be provided for receiving and engaging the outer rim of the cap to enclose the entire cap interior and to seal so as to maintain a sterile interior. In one embodiment, a blind fitting is formed on the valve body. In another embodiment, a modified Luer cap having a blind extension thereon is mounted on a Luer fitting of a valve such that the blind extension of the cap can receive and store an out-of-use cap. In another embodiment, a cap storage member having plural blind extensions may be slidably attached to and detached from a valve.

Various patents have also issued in the past relating to various fluid control valves that have cam-controlled movement. For example, U.S. Pat. No. 4,865,078, issued on Sep. 12, 1989 to Ensign, describes a manual control valve. The manual control valve employs a compact body, a pressure input port and first and second output ports to which are secured tubular seat housings, each carrying a valve seat. First and second poppets are slidably mounted in the tubular seat housings and are spring urged to closed position. One or the other of the poppets is pulled open by means of a handle operated rotary cam, which allows both poppets to be closed by spring and water pressure. A modified valve configuration provides a three-way valve.

U.S. Pat. No. 4,632,361, issued on Dec. 30, 1986 to Callison, teaches a scheduled fluid control valve. The scheduled fluid control valve performs a pre-established sequence of flow rates and timing schedules in response to pressure pulses in the controlled fluid. The valve consists of a generally cylindrical housing connected to a source of pressurized fluid and containing circular plates of cylindrical control surfaces coupled to actuating means responsive to the presence of pressurized fluid. The actuating means includes an actuator plate or cylinder, a biasing spring, and a longitudinal shaft or cylinder upon which is incised at least one generally helical groove within which track one or more follower pins. Pressurized fluid causes the actuator plate or cylinder to rotate, following the path defined by the helical groove, resulting in relative movement of the control surfaces whereby the schedule embodied in the relative size and placement of fluid ports through the control surfaces is performed. A plurality of control surfaces may be substituted to select a large number of fluid flow schedules and flow rates.

Various patents have issued relating to valves that move up and down so as to provide access to the various ports. For example, U.S. Pat. No. 4,570,674, issued on Feb. 18, 1986 to Kaye, describes a mechanically-programmable sequencing valve. The sequencing valve assembly is used for controlling plural fluid-operated motors. It includes a series of valve housing modules, sealably joined to one another thereby forming an elongate valve housing, which receives plural valve inserts. The valve housing modules collectively form manifolds, which may be connected to a pressurized source of fluid and an exhaust line. The assembly is mechanically programmable and provides a visible, non-volatile program to control multiple motors. Individual valves are actuated by cam-operated rocker arms. A camshaft includes removable adjustable cams, and this assembly may be quickly changed by replacing or rearranging the shaft, its associated cams, or nodules on the cams.

Various patents have also issued relating conventional stopcocks with rotatable knobs for the purpose of aligning the various fluid passageways. For example, U.S. Pat. No. 4,003,403, issued on Jan. 18, 1977 to Nehring, describes such a stopcock. The stopcock has a body suitable for molding, having an axial bore, axially and angularly spaced apart inlet and outlet passageways through the body and intersecting the bore, and a stem rotatably mounted within the bore, the stem having an elongated slot extending radially partially therethrough and a port angularly spaced from the intersection of the slot and the stem surface and intersecting the slot at the interior of the stem. The stem is rotatable from a position effecting fluid flow communication between the passageways to a position obstructing at least one of the passageways. Vent means are provided to permit removal of all liquid from the passageways.

U.S. Pat. No. 3,834,372, issued on Sep. 10, 1974 to Turney, describes a disposable manifold with an atmospheric vent. The manifold is formed with a plurality of ports for connection to various components such as arterial-venous pressure generators, a syringe, and a source of fluid and pressure sensitive transducers. The manifold includes one or more rotary members, which are selectively positioned for interconnecting selected ones of the components. Various sampling, flushing and pressure measuring operations may be performed by use of the manifold. The manifold further includes a venting port arrangement for venting the pressure sensitive transducers to the atmosphere when a pressure measurement is not being taken. This protects the transducer from overpressurization and consequential damage.

Traditionally, plural infusion tubes are used to supply fluids such as drug solutions into a patient's body. In cases like this, medical stopcocks are used to allow the solutions to communicate between each infusion tube or shut-off the communication. Among the prior art stopcocks, there exist medical stopcocks capable of allowing an operator to open or shut-off the communication between each branch-tube and the chamber part by moving the operating part in the axial direction of the chamber part, wherein the chamber part has a cylindrical shape. The medical stopcock disclosed in this prior art is formed in such a manner that 2 branch-tubes are provided interposing the peripheral surface of an approximately cylindrically shaped chamber part, and the valve body in the axial direction in the chamber part can be rotated to open and close the communication between the 2 branch-tubes.

However, this medical stopcock is provided with only 2 branch-tubes, and only capable of simply allowing one to open or shut-off the communication between the 2 branch-tubes. Hence, this medical stopcock cannot be connected to plural lines of infusion tubes and analogs used for medical purposes to switch the communication and shut-off statuses of each infusion tube. Moreover, in order to allow the 2 branch-tubes to communicate with one another or shut-off the communication with one another, the rotational manipulation of the valve body must be performed, posing a difficulty to operate. Consequently, the medical stopcock comprising 3 branch-tubes, capable of switching the flow passage by performing the rotational manipulation of the cock in the axial direction of the valve body has also been developed. However, even in such a medical stopcock, during the manipulation, the main body of the medical stopcock needs to be held by one hand, and the cock needs to be manipulated by the other hand, and therefore it is difficult to operate.

Various patents and patent publications have attempted to address the problem of multiple branch tubes, and ease of use. For example, U.S. Patent Publication No. 2008/0319401 published on Dec. 25, 2008 to Funamura, describes such a stopcock valve. The stopcock allows easier switching operation of plural branch-tubes. The main body of the stopcock comprises a chamber part with a nearly spherical inner surface, and an upstream branch-tube, a downstream branch-tube and a merge-branch-tube all extending from the chamber part. A valve body of the stopcock comprises a nearly spherical valve main body and a rod-shaped operating part with a guide hole linking the inner surface of the chamber part to the outside. In operation, the rod-shaped operating part is moved along the guide hole through the use of the horizontal flow passages and the vertical flow passage to allow the predetermined branch-tubes out of the upstream branch-tube, the downstream branch-tube and the merge-branch-tube to communicate with one another or to shut-off the communication.

It is an object of the present invention to provide a pushbutton stopcock assembly which is easy to manufacture and inexpensive.

It is another object of the present invention to provide a disposable pushbutton stopcock assembly.

It is a further object of the present invention to provide a pushbutton stopcock assembly, which is easy to operate and requires the use of only one hand.

It is another object of the present invention to provide a stopcock assembly, having a pushbutton mechanism.

It is still another object of the present invention to provide a pushbutton stopcock assembly with variable selectable flow paths.

It is another object of the present invention to provide a pushbutton stopcock assembly with three separate flow paths.

It is yet another object of the present invention to provide a pushbutton stopcock assembly with easily identified flow path selections.

These and other objects and advantages of the present invention will become apparent from a reading of the attached specification and appended claims.

SUMMARY OF THE INVENTION

The present invention is a pushbutton stopcock assembly having a sleeve with a plurality of outer ports, a body portion with a plurality of inner ports corresponding to the outer ports, and a pushbutton to actuate a rotation of the body portion so as to align and misalign the inner and outer ports. Each outer port of the sleeve connects to a fluid passageway for the introduction of fluids, and each outer port is arranged perpendicular to at least one adjacent outer port. The body portion is housed within the sleeve along a shared rotational axis. The body portion has a first end with a spring, wherein the first end is inserted into the sleeve. The body portion has a second end with a cam means. Each inner port of the body portion is arranged perpendicular to at least one adjacent inner port, and each inner port is in fluid connection with the other inner ports. In this manner, the fluids flow and travel from fluid passageways, through the outer ports, and through the inner ports. The pressure of the fluid from each fluid passageway determines the direction of flow.

The pushbutton abuts the second end portion of the body portion, such that depressing the pushbutton engages the cam means of the body portion. The cam means is cooperative with a complementary cam means within the sleeve so as to rotate the body portion a set amount and direction. Each set amount of rotation corresponds to a particular alignment of the outer ports and inner ports. In this manner, a simple button push changes the fluid flow connections in the stopcock assembly without requiring two hands or manual adjustment of the rotation. The stopcock assembly can have three outer ports and two inner ports. Alternatively, the assembly may have three outer ports and three inner ports. The combination of fluid connections can be marked on the pushbutton for indicating the alignment of the inner and outer ports. Luer lock adapters in the fluid passageways allow the stopcock assembly to be set before fluid is released and flowed through the assembly.

DETAILED DESCRIPTION OF THE DRAWINGS

Figure 1:
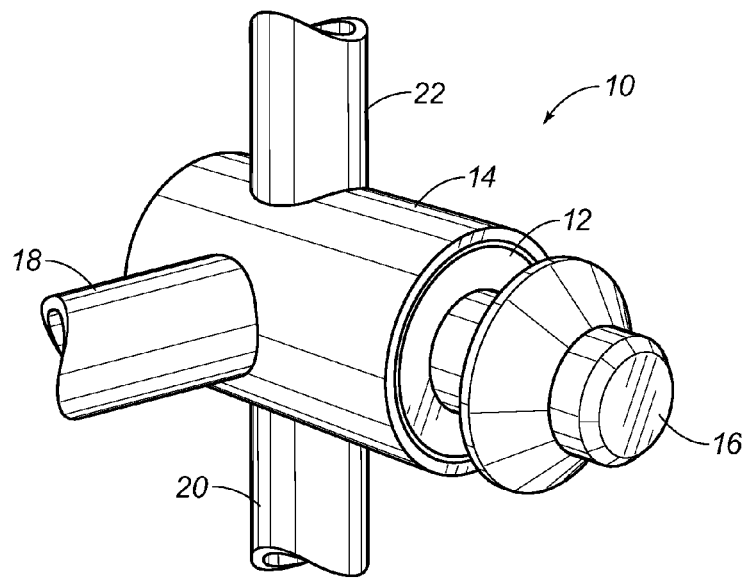
FIG. 1 is a top plan view of the pushbutton stopcock assembly of the present invention.
Figure 2:
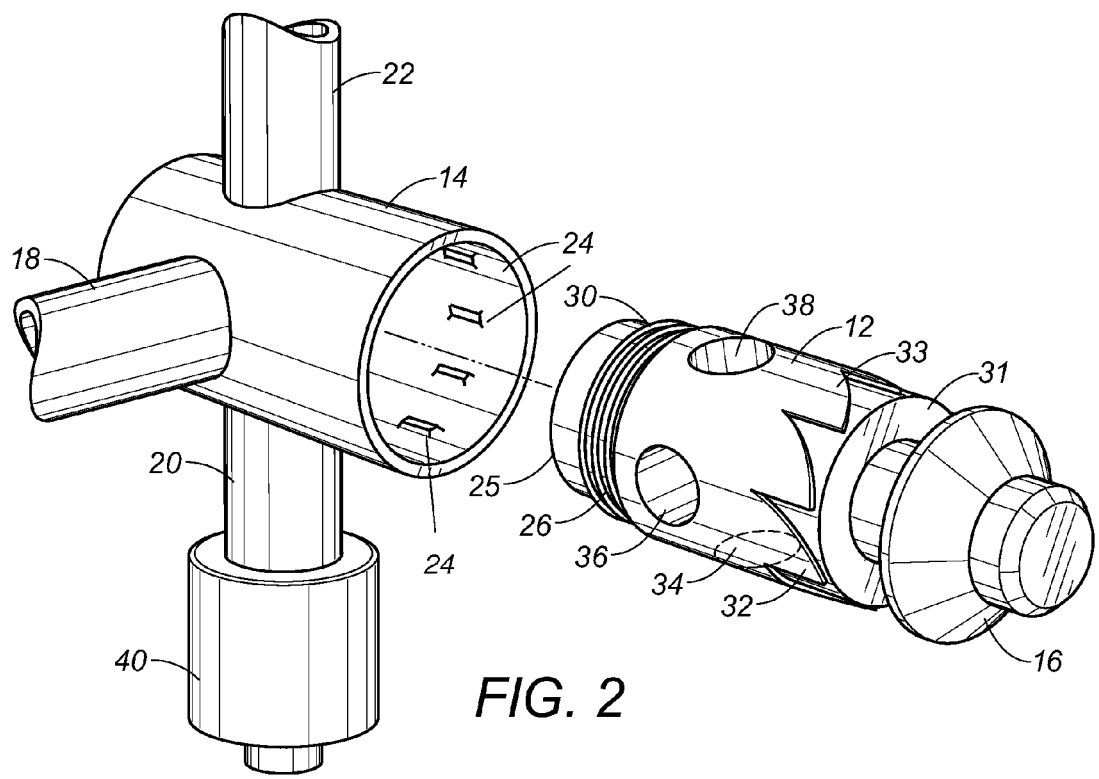
FIG. 2 is an exploded side elevation view of the pushbutton stopcock assembly of the present invention.

Referring to FIG. 1, there is shown the pushbutton stopcock assembly 10 in the preferred embodiment of the present invention. The pushbutton stopcock assembly 10 has a sleeve 14 and a body portion 12, each having a cylindrical configuration. The body portion 12 is received within the interior of the sleeve 14. The body portion 12 is connected to a pushbutton 16. The sleeve 14 has a plurality of outer ports, shown as a first outer port 18, a second outer port 20 and a third outer port 22, in FIGS. 1 and 2. The three outer ports 18, 20 and 22 extend outwardly from the sleeve 14 and connect to fluid passageways, as shown in FIG. 2. Each of the outer ports 18, 20 and 22 are arranged on an axis perpendicular to each other or at least one adjacent outer port.

The body portion 12 is shown in greater detail in FIG. 2. The body portion 12 is similarly cylindrical for being inserted within the sleeve 14. The body portion 12 has a first end portion 25 with a spring 26 affixed thereon and a second end portion 31 with a cam means 32. The first end portion 25 with the spring 26 has a smaller diameter that the body portion 12. There are a plurality of inner ports, shown as a first inner port 34, second inner port 36 and third inner port 38. Similar to the outer ports, the inner ports 34, 36 and 38 are arranged on an axis perpendicular to each other or at least one adjacent inner port. Also, the inner ports correspond to the locations of the outer ports. The inner ports 34, 36 and 38 extend partially through the body portion 12 and are in fluid communication with each other.

Figure 5:
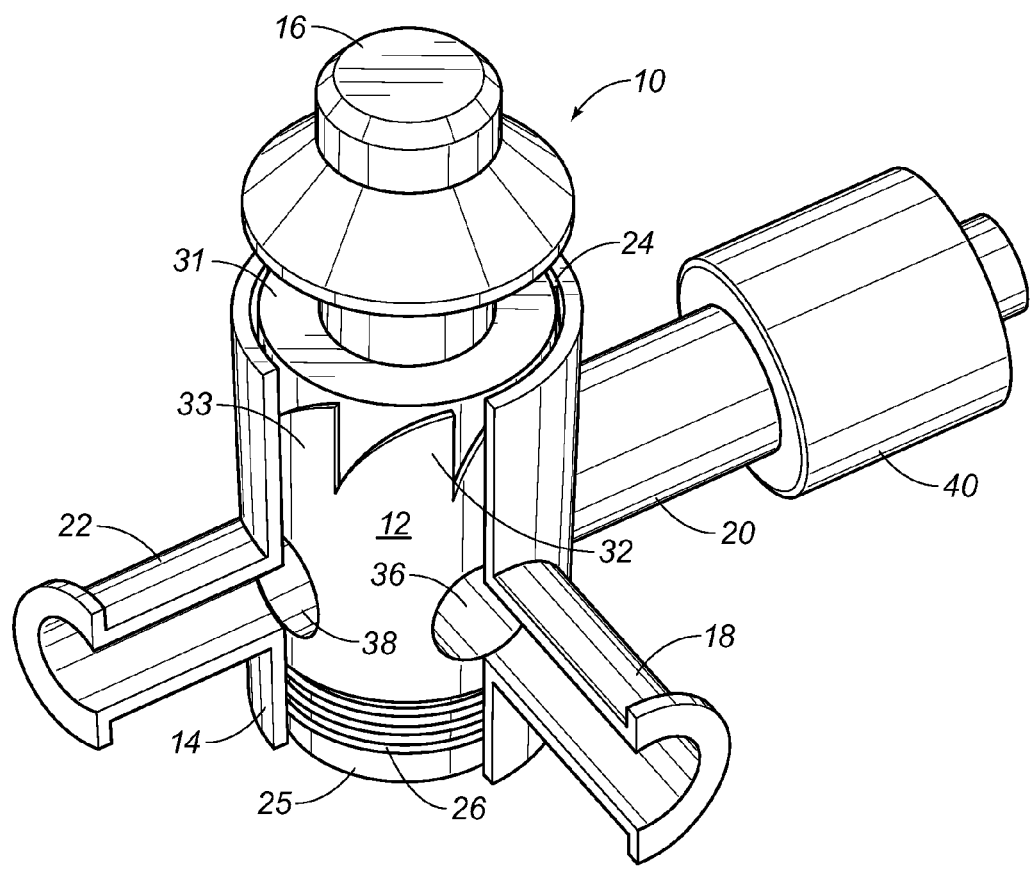
FIG. 5 is a partial sectional view and partial perspective view of the pushbutton stopcock assembly of the present invention.

The pushbutton 16 is shown in FIGS. 1, 2 and 5. The pushbutton 16 moves between an extended position to a depressed position, and the spring 26 returns the pushbutton 16 from the depressed position to the extended position.

FIGS. 2 and 5 also show the cam means 32 of the body portion 12. The interior of the sleeve 14 has a complementary cam means 24. The cam means 32 and the complementary cam means 24 are cooperative so as to rotate the body portion 12 about an axis aligned with the sleeve 14. The pushbutton 16 engages the cam means 32 when moving from the extended position to the depressed position such that the cam means 32 and the complementary cam means 24 rotate the body portion 12 a set amount and direction about the axis aligned with the sleeve 14. Each click from extended position to depressed position causes a rotation about the axis either clockwise or counterclockwise. The alignment between the inner ports 34, 36, and 38 and the outer ports 18, 20, and 22 corresponds to the set amount of rotation of the body portion. As such, by rotating the body portion 12, the inner and outer ports can be aligned and unaligned so as to selectively allow fluids or gas to pass through the selected inner and outer ports.

Also shown in FIG. 2 is the Luer lock connection 40 on the first outer port 18. Through Luer lock connection 40 is commonly used in medical devices and allows for a secure connection to sources of fluids or gases. The Luer lock connection 40 shown in FIG. 2 is a female connector, which corresponds to a male connection from a source of fluid. Similar connections can be provided on second outer port 20 and third outer port 22. The Luer lock connection 40 is important to allow the stopcock assembly 10 to set the alignment of the ports before the fluid connections are made so as to insure dispensing the proper fluids through the proper passageways.

Figure 3:
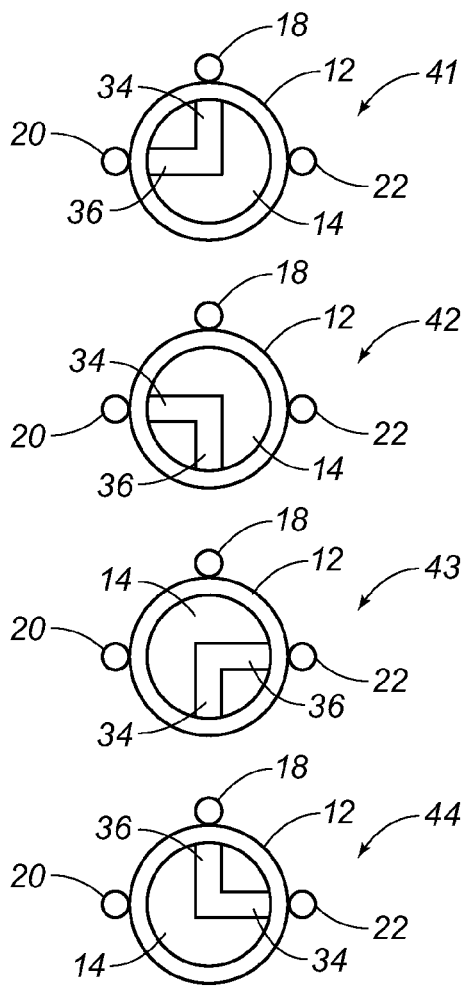
FIG. 3 is a schematic view showing the position of the body portion where the body portion has two inner ports.
Figure 4:
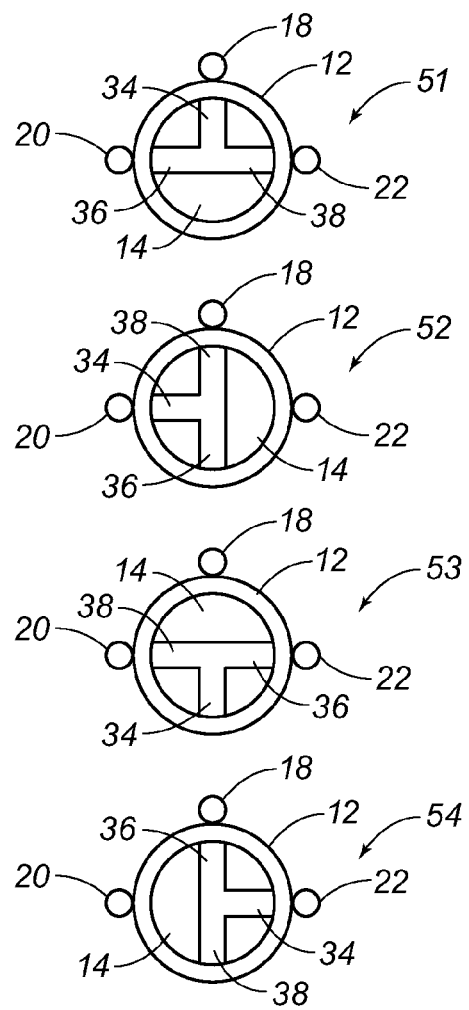
FIG. 4 is a schematic view showing the position of the body portion where the body portion has three inner ports.

FIGS. 3 and 4 show embodiments of the present invention. The plurality of outer ports and plurality of inner ports can be combined into different alignments for different applications. The pushbutton 16 can be marked so that a particular alignment corresponded to a marker on the front of the pushbutton 16. In this manner, the configuration of the inner ports and outer ports can be visually detected in an easy manner. For example, the pushbutton 16 may show 1-1 and 2-2 at the top, indicating that the first inner port is aligned with the first outer port and that the second inner port is aligned with the second outer port. The pushbutton 16 may show 1-0 and 2-1 rotated to the top, indicating that the first inner port is aligned with a stop and that the second inner port is aligned with the first outer port. As such, the user may coordinate the connections to the fluid passageways as appropriate and without clicking the pushbutton 16 when guessing the alignment.

FIG. 3 shows a schematic view of an embodiment with a first outer port 18, a second outer port 20, a third outer port 22, and a plurality of inner ports comprised of a first inner port 34, and a second inner port 36. FIG. 3 shows an initial alignment 41 with the first inner port 34 corresponding to the first outer port 18 and the second inner port 36 corresponds to the second outer port 20 after rotation of the set amount of the body portion 12. The fluid flows between the fluid passageways associated with outer port 18 and outer port 20, and the fluid can be dispensed accordingly, such as an IV drip (outer port 18) into a patient fluid line (outer port 20).

After a subsequent rotation by depressing the pushbutton 16, the body portion 12 rotates the set amount for second alignment 42, as shown in FIG. 3. The first inner port 34 corresponds to the second outer port 20, and the second inner port 36 corresponds to a stop in misalignment. The fluid does not flow between any outer port, so this alignment can be labeled as an off position.

Still another rotation of the perpendicular ports can be caused by depressing the pushbutton 16 again to a third alignment 43 of FIG. 3. The first inner port 34 corresponds to the stop, and the second inner port 36 corresponds to the third outer port 32 in misalignment. Fluid does not flow between any outer port, so this alignment is also labeled as an off position.

The next rotation by depressing the pushbutton 16 results in a fourth alignment 44 of FIG. 3. The first inner port 34 corresponds to the third outer port 22, and the second inner port 36 corresponds to the first outer port 18, after this still another subsequent rotation of the set amount of the body portion 12. Fluid flows between outer port 18 and outer port 22, so that the connections to a fluid source can be made according to this alignment. Another set amount of rotation returns the first inner port 34 to the first outer port 18 and the second inner port 36 to the second outer port 20.

FIG. 4 shows a schematic view of an embodiment with a first outer port 18, a second outer port 20, a third outer port 22, and a plurality of inner ports comprised of a first inner port 34, a second inner port 36, and a third inner port 38. FIG. 4 shows an initial alignment 51 with the first inner port 34 corresponding to the first outer port 18, the second inner port 36 corresponds to the second outer port 20, and the first inner port 38 corresponds to the third outer port 22 after rotation of the set amount of the body portion 12. The fluid flows between the fluid passageways associated with outer ports 18, 20 and 22, and the fluid can be dispensed accordingly, such as an IV drip (outer port 18) and an additive drip (outer port 22) into a patient fluid line (outer port 20). Two fluids can be dispensed to the patient through a single stopcock assembly 10 of the present invention.

After a subsequent rotation by depressing the pushbutton 16, the body portion 12 rotates the set amount for second alignment 52, as shown in FIG. 4. The first inner port 34 corresponds to the second outer port 20, the second inner port 36 corresponds to a stop, and the third inner port 38 corresponds to the first outer port 18. Even with the stop, fluid still flows in this configuration, i.e. fluid flows between the first outer port 18 and the second outer port 20, using different inner ports. The fluid source connections can be adjusted for this alignment of the outer ports 18 and 20.

Still another rotation of the perpendicular ports can be caused by depressing the pushbutton 16 again to a third alignment 53 of FIG. 4. The first inner port 34 corresponds to the stop, the second inner port 36 corresponds to the third outer port 32, and the third inner port 38 corresponds to the second outer port 20. In this orientation, fluid flows between the second and third outer ports using different inner ports through the body portion 12. Again, the fluid source connections adjust according to this connection through the stopcock assembly 10 of the present invention.

The next rotation by depressing the pushbutton 16 results in a fourth alignment 54 of FIG. 4. The first inner port 34 corresponds to the third outer port 22, the second inner port 36 corresponds to the first outer port 18, and the third inner port 38 corresponds to the stop after this still another subsequent rotation of the set amount of the body portion 12. Fluid flows between outer port 18 and outer port 22, so that the connections to a fluid source can be made according to this alignment. Another set amount of rotation returns the inner ports and outer ports to their initial alignment 51.

As shown in FIGS. 2 and 5, the cam means 32 comprises a plurality of engagement means 33, each engagement means 33 being arranged for a set amount and direction of rotation of the body portion 12. The engagement means 33 can be shaped as teeth or prongs or pegs according to the amount and direction of rotation. For example, a single "click" or depression and return of the pushbutton 16 from the extended position to the depressed position and back to the extended position by the spring 26 can result in a 45 degree clockwise rotation. The teeth may be respectively slanted for the clockwise or counterclockwise direction or curved for rotation in both directions. In any case, the perpendicular ports are rotated in coordination with the cam means 32. Although FIGS. 2 and 5 show slanted teeth for 45 degree rotation with each click, teeth, prongs or other structures can be used for the engagement means 33 of the cam means 32, as long as cooperative with the complementary cam means 24. Another example is four 90 degree clockwise rotation, matching four positions of the ports. Each click would rotate 90 degrees clockwise to change the alignment of ports in single clicks. A single click is not always ideal, so the engagement means 32 can adjust for alternate parameters. FIGS. 2 and 5 do not even show the complementary cam means 24, which includes any fixed structure in the sleeve 14 to abut the cam means 32. The complementary cam means 24 may include a plurality of protrusions within the sleeve 14, being spaced at along the circumference of the sleeve 14 and engaging respective engagement means 33. The complementary cam means 24 does not move or rotate, forcing the cam means 32 on the body portion 12 to move. These structures can be shaped to complement the teeth or blocks or prongs of the engagement means 33 so as to rotate the body portion 12 a set amount and direction as the pushbutton 16 moves from the extended position to the depressed position. The spring 26 snaps the pushbutton 16 back to its extended position for a subsequent action.

FIG. 5 shows the alignment 51 of the top diagram of FIG. 4. FIG. 5 shows the initial alignment 51 with the first inner port 34 corresponding to the first outer port 18, and the first inner port 38 corresponds to the third outer port 22 after rotation of the set amount of the body portion 12. The second inner port 36 (not shown) corresponds to the second outer port 20.

The method of controlling fluid flow with the pushbutton stopcock assembly 10 of the present invention includes connecting fluid passageways to a plurality of outer ports on a sleeve of the stopcock, pressing a pushbutton to engage a cam on the end of a body portion of the stopcock within the sleeve, and rotating the body portion on an axis aligned with the sleeve. Each fluid passageway can be sealed to attach to a respective outer port as a fluid source, and the body portion has a plurality of inner ports, which rotate into fluid connection with the fluid sources for dispensing fluid. The cam is cooperative with a complementary cam within the sleeve to control the amount of rotation, and the inner ports of the body portion are aligned with outer ports of the sleeve so as to selectively allow fluids or gas to pass through corresponding outer ports and inner ports.

The pushbutton is used to compress a spring on a first end of the body portion within the sleeve and to engage the cam for restricted rotation. The compression when the cam and the complementary cam stop rotation of the body portion. Then, the spring releases the pushbutton to return to an original extended position, the body portion being locked in a rotated state. Alignment or misalignment of corresponding outer ports and inner ports are locked in place when the pushbutton returns to the original position.

The use of the pushbutton stopcock assembly 10 in the present invention is relatively easy to operate compared to the prior art. A conventional system utilizing a stopcock, requires a physician or other treating professional to use both hands in order activate the stopcock. One hand would have to be used to stabilize the body of the stopcock, while the other hand would have to be used to turn the traditional handle to open and close fluid passageways. In the present invention, the pushbutton stopcock assembly 10 can be easily used with one hand. A physician or treating professionals can stabilize the body of the stopcock 14 with only two fingers, while depressing the pushbutton 16 with his or her thumb or alternate finger. This allows the treating professional or physician to easily selectively allow for the passage of fluid through the fluid passageways. Also, the perpendicular standardization eliminates the manual adjustment of aligning the inner ports and outer ports. The user does not have to guess or continually manipulate the body portion in order to insure the proper and full fluid connection between the outer ports. That is, the pushbutton sets the amount of rotation instead of the possibility of half-open or half-rotated alignment. The one-handed actuation maximizes quick and efficient movements for operating room use, which are important benefits over the prior art. The automated alignment by set amounts of rotation allows the flow rates to be standardized for predictable results and more controlled fluid dispensing. A partially-opened flow path, due to an offset inlet port and outlet port is avoided by the present invention.

Additionally, the pushbutton is easier to manufacture. The structures and perpendicular orientation are more uniform for multiple fluid passageways. The costs are less expensive than variable inlets and outlets for each bulb of the traditional stopcock. The proper labeling and marking of the orientation of the ports enable a more efficient and less costly stopcock to be used, such that the stopcock assembly may be disposable. Multiple fluid sources can be connected to the outer ports, and the labeling of the pushbutton of the stopcock assembly can clearly indicate which ports connect to which other ports. With the prior art, there is only an off position indicator. The user must carefully examine the stopcock to see the outlet port and inlet port alignments as the body portion is rotated. With multiple inlet ports and outlet ports, the user must carefully review the entire stopcock to insure that the proper ports are aligned for the desired connections of the flow path. The present invention allows for marking the four orientations of the body portion on the button. Because orientation of the button corresponds to a particular flow path pattern, visual and/or tactile markings can be strategically placed on the pushbutton to indicate the flow path pattern to a user, without requiring the extra examination of the body portion. For example, in FIG. 4, alignment 51 for connecting flow between all three outlet ports can be indicated by a symbol on the pushbutton, and alignment 53, for connecting flow between the second and third outlet ports can be indicated by a different symbol on the pushbutton, so that the symbol identifies the flow pattern. The user can press the pushbutton until the desired flow path is set by the present invention, instead of looking around the entire stopcock assembly each time. With Luer locks, the stopcock of the present invention can remain cleared for rotating the body portion, such that there is no fluid flow until the correct orientation is set in place. The change between different flow paths and different sources can be economically and ergonomically controlled by a single pushbutton of the present invention.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A pushbutton stopcock assembly, comprising:
    a sleeve, being cylindrical and having a plurality of outer ports, each outer port extending outward from said sleeve and being connectable to fluid passageways, each outer port being arranged perpendicular to at least one adjacent outer port;
    a body portion, being cylindrical and received within an interior of said sleeve, said body portion having a spring affixed on a first end portion thereof and a cam means on a second end portion, said first end portion having a diameter smaller than other portions of said body portion, said body portion having a plurality of inner ports corresponding to said plurality of outer ports, said inner ports being in fluid communication with each other and being arranged perpendicular to at least one adjacent inner port, each inner port extending partially through said body portion; and
    a pushbutton, being connected to said body portion at said second end portion thereof,
    wherein said cam means is cooperative with a complementary cam means within said sleeve so as to rotate said body portion about an axis aligned with said sleeve,
    wherein said pushbutton moves between an extended position to a depressed position, said spring returning said pushbutton from said depressed position to said extended position, said pushbutton engaging said cam means when moving from said extended position to said depressed position such that said cam means and said complementary cam means rotate said body portion a set amount and direction about said axis aligned with said sleeve, and
    wherein alignment between said inner ports on said body portion and said outer ports on said sleeve corresponds to the set amount of rotation of said body portion.

2. The pushbutton stopcock assembly of claim 1, wherein an outer port of said sleeve has a Luer lock at a distal end thereof.

3. The pushbutton stopcock assembly of claim 1, wherein said plurality of outer ports comprise a first outer port, a second outer port, and a third outer port, and wherein said plurality of inner ports comprise a first inner port, and a second inner port.

4. The pushbutton stopcock assembly of claim 3, wherein said first inner port corresponds to said first outer port and said second inner port corresponds to said second outer port in alignment after rotation of said set amount of said body portion,
    wherein said first inner port corresponds to said second outer port and said second inner port corresponds to a stop in misalignment after a subsequent rotation of said set amount of said body portion,
    wherein said first inner port corresponds to said stop and said second inner port corresponds to said third outer port in misalignment after another subsequent rotation of said set amount of said body portion,
    wherein said first inner port corresponds to said third outer port and said second inner port corresponds to said first outer port in alignment after still another subsequent rotation of said set amount of said body portion, and
    wherein another set amount of rotation returns said first inner port to said first outer port and said second inner port to said second outer port.

5. The pushbutton stopcock assembly of claim 1, wherein said plurality of outer ports comprise a first outer port, a second outer port, and a third outer port, and wherein said plurality of inner ports comprise a first inner port, a second inner port, and a third inner port.

6. The pushbutton stopcock assembly of claim 5, wherein said first inner port corresponds to said first outer port, said second inner port corresponds to said second outer port, said third inner port corresponds to said third outer port in alignment after rotation of said set amount of said body portion,
    wherein said first inner port corresponds to said second outer port, said second inner port corresponds to a stop, said third inner port corresponds to said first outer port in alignment after a subsequent rotation of said set amount of said body portion,
    wherein said first inner port corresponds to said stop, said second inner port corresponds to said third outer port, said third inner port corresponds to second outer port in alignment after another subsequent rotation of said set amount of said body portion,
    wherein said first inner port corresponds to said third outer port, said second inner port corresponds to said first outer port, said third inner port corresponds to said stop in alignment after still another subsequent rotation of said set amount of said body portion, and
    wherein another set amount of rotation returns said first inner port to said first outer port, said second inner port to said second outer port, and said third inner port to said third outer port.

7. The pushbutton stopcock assembly of claim 1, wherein said cam means comprises a plurality of engagement means, each engagement means being arranged for 90 degree rotation of said body portion for each actuation of said pushbutton,
   wherein said complementary cam means comprises a plurality of protrusions within said sleeve engaging respective engagement means, and
   wherein each protrusion engages a respective engagement means to rotate said body portion a set amount as said pushbutton moves from said extended position to said depressed position in a set direction.

8. The pushbutton stopcock assembly of claim 7, wherein each protrusion engages an adjacent engagement means, when said spring returns said pushbutton to said extended position.

\* \* \* \* \*